(12) United States Patent
Ueda et al.

(10) Patent No.: US 7,524,993 B2
(45) Date of Patent: Apr. 28, 2009

(54) METHOD OF PRODUCING REDUCED COENZYME $Q_{10}$ AS OILY PRODUCT

(75) Inventors: Takahiro Ueda, Hyogo (JP); Shiro Kitamura, Hyogo (JP); Yasuyoshi Ueda, Hyogo (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 11/716,828

(22) Filed: Mar. 12, 2007

(65) Prior Publication Data

US 2007/0161825 A1 Jul. 12, 2007

Related U.S. Application Data

(62) Division of application No. 10/483,870, filed as application No. PCT/JP02/07145 on Jul. 15, 2002, now Pat. No. 7,208,639.

(30) Foreign Application Priority Data

| Jul. 13, 2001 | (JP) | ............................... 2001-214475 |
| Jul. 13, 2001 | (JP) | ............................... 2001-214480 |
| Apr. 17, 2002 | (JP) | ............................... 2002-114873 |
| Apr. 17, 2002 | (JP) | ............................... 2002-114875 |

(51) Int. Cl.
*C07C 41/18* (2006.01)

(52) U.S. Cl. .................. 568/652; 568/654; 568/662

(58) Field of Classification Search ................ None
See application file for complete search history.

(56) References Cited

U.S. PATENT DOCUMENTS

| 3,068,295 A | 12/1962 | Folkers et al. ............... 568/654 |
| 6,184,255 B1 | 2/2001 | Mae et al. .................. 514/720 |
| 7,105,709 B2 | 9/2006 | Ueda et al. ................. 568/823 |
| 2004/0236154 A1 | 11/2004 | Ueda et al. .................. 568/668 |

FOREIGN PATENT DOCUMENTS

| GB | 947643 A | 1/1964 |
| JP | 52-072 884 A | 6/1977 |
| JP | 52-72884 A | 6/1977 |
| JP | 53-133687 | 11/1978 |
| JP | 53-133687 A | 11/1978 |
| JP | 56-92238 A | 7/1981 |
| JP | 57-70834 A | 5/1982 |
| JP | 60-75294 | 4/1985 |
| WO | WO 96/17626 A2 | 6/1996 |

OTHER PUBLICATIONS

International Search Report From Corresponding International Application No. PCT/JP02/07145, Dated Oct. 21, 2002, 4 Pages.
Patent Cooperation Treaty International Preliminary Examination Report (PCT Article 36 and Rule 70), From Corresponding International Application No. PCT/JP02/07145, Dated May 28, 2003, 5 Pages.

*Primary Examiner*—Rosalynd Keys
(74) *Attorney, Agent, or Firm*—Brinks Hofer Gilson & Lione

(57) ABSTRACT

The present invention provides a method for obtaining reduced coenzyme $Q_{10}$ which is useful as an ingredient in foods, functional nutritive foods, specific health foods, nutritional supplements, nutrients, drinks, feeds, cosmetics, medicines, remedies, preventive drugs, etc. suited for a commercial scale production in high quality and efficiently. The high-quality oily reduced coenzyme $Q_{10}$ which has low viscosity and thereby easily handled may be produced by separating an aqueous phase from the reaction mixture obtainable by oily reacting oxidized coenzyme $Q_{10}$ with a reducing agent in water, or by distilling off an coexisting organic solvent at or above the melting temperature of reduced coenzyme $Q_{10}$ in concentrating the organic phase containing reduced coenzyme $Q_{10}$. Moreover, a solution or slurry of reduced coenzyme $Q_{10}$ may be obtained by adding a desired solvent to the obtained oily product, or a solid of reduced coenzyme $Q_{10}$ may be produced by contacting the oily product with a seed crystal.

15 Claims, No Drawings

METHOD OF PRODUCING REDUCED COENZYME $Q_{10}$ AS OILY PRODUCT

RELATED APPLICATIONS

This application is a division of application Ser. No. 10/483,870, filed Jul. 2, 2004, now U.S. Pat. No. 7,208,639, the latter of which is a nationalization of PCT Application No. PCT/JP02/07145, filed Jul. 15, 2002. This application claims priority from Japanese Patent Application No. 2001-214475 filed on Jul. 13, 2001; Japanese Patent Application No. 2001-214480 filed on Jul. 13, 2001; Japanese Patent Application No. 2002-114873 filed on Apr. 17, 2002; and Japanese Patent Application No. 2002-114875 filed on Apr. 17, 2002.

BACKGROUND

1. Technical Field

The present invention relates to a method of producing reduced coenzyme $Q_{10}$. Reduced coenzyme $Q_{10}$ shows a higher level of oral absorbability as compared with oxidized coenzyme $Q_{10}$ and is a compound useful as an ingredient in good foods, functional nutritive foods, specific health foods, nutritional supplements, nutrients, drinks, feeds, cosmetics, medicines, remedies, preventive drugs, etc.

2. Background Information

It is known that reduced coenzyme $Q_{10}$ can be prepared by producing coenzyme $Q_{10}$ in the conventional manner, for example by synthesis, fermentation, or extraction from natural products, and concentrating a reduced coenzyme $Q_{10}$-containing eluate fraction resulting from chromatography (JP-A-10-109933). On that occasion, as described in the above-cited publication, the chromatographic concentration may be carried out after reduction of oxidized coenzyme $Q_{10}$ contained in the reduced coenzyme $Q_{10}$ with a conventional reducing agent such as sodium borohydride or sodium dithionite (sodium hyposulfite), or reduced coenzyme $Q_{10}$ may be prepared by reacting the reducing agent mentioned above with an existing highly pure grade of coenzyme $Q_{10}$.

JP-A-57-70834 discloses an example in which reduced coenzyme $Q_{10}$ was synthesized by dissolving coenzyme $Q_{10}$ in hexane and adding an aqueous solution of sodium hydrosulfite (sodium hyposulfite) in an amount of twice the weight of coenzyme $Q_{10}$ to the solution, followed by stirring.

However, the conventional methods require operations such as extraction of the generated reduced coenzyme $Q_{10}$ with an organic solvent and concentration, thus the process time becomes inevitably long, and also require an expensive production apparatus and large capacity.

Moreover, when trying to distilling off a solvent from an organic phase containing reduced coenzyme $Q_{10}$ reduced coenzyme $Q_{10}$ precipitates in the form of semi-solid or solid during the operation, which leads to troublesome conditions such as increase of stirring load and stirring failure, and as a result, the solvent removal tends to be incomplete. Generally, this phenomenon tends to become marked when the purity of reduced coenzyme $Q_{10}$ is high.

Such characteristic of reduced coenzyme $Q_{10}$ causes a problem not only in isolating reduced coenzyme $Q_{10}$ but also in preparing a solution or slurry of reduced coenzyme $Q_{10}$ prepared by substituting the solvent of the organic phase mentioned above with another solvent, such as the case of carrying out crystallization. The solvent substitution requires such a complicated operation as repeating a solvent removal process with supplementing a solvent, thus, problems are caused on the commercial scale such as workability, cost efficiency and quality, as described below.

In the case of substituting a solvent having a high-boiling point into a solvent having a low-boiling point or the case that solvents to be used each other form an azeotrope, solvent substitution becomes an extremely inefficient process which consumes much solvent and a lot of time. Additionally, unfavorable components or impurities, which coexists in the solvent to be supplemented (e.g. high-boiling point components or hardly volatile components) accumulate in the solution in a high concentration. For example, as in a case of substitution of a heptane solution having a high boiling point to a tetrahydrofuran solution having a low boiling point, the solvent substitution becomes an extremely inefficient, and there is a possibility that stabilizers such as 2,6-di-tert-butyl-4-hydroxytoluene (BHT), which coexists in tetrahydrofuran, accumulate in the solution in a high concentration more than necessity.

Moreover, reduced coenzyme $Q_{10}$ is readily oxidized into oxidized coenzyme $Q_{10}$ by molecular oxygen. On a commercial production scale, complete oxygen elimination is very difficult to achieve and, furthermore, fairly long periods of time are required for individual operations, unlike laboratory scale production, so that residual oxygen exerts a great adverse effect. The oxidation in question is directly connected with such yield and quality problems as the formation of hardly eliminable oxidized coenzyme $Q_{10}$ and immixture into the product. For obtaining highly pure reduced coenzyme $Q_{10}$ it is preferable to shorten the operation time for such as concentration and solvent substitution in view of adequate protection of the reduced form from the oxidation mentioned above.

Therefore, it has been desired a method for directly and easily obtaining reduced coenzyme $Q_{10}$ without requiring additional operations such as extraction with an organic solvent and concentration, etc., and/or a method for distilling off an organic solvent from the organic phase containing reduced coenzyme $Q_{10}$ in a convenient manner and in a short time, without causing stirring failure.

SUMMARY OF THE INVENTION

In view of the foregoing, the present invention has an object to provide a method suited for commercial scale production and can give high-quality reduced coenzyme $Q_{10}$ in a convenient and efficient manner.

As a result of intensive investigations, the present inventors unexpectedly found that the high-quality reduced coenzyme $Q_{10}$ can be produced by reacting oily oxidized coenzyme $Q_{10}$ with a reducing agent in water, and thereby completed the present invention useful for the production on the commercial scale. The inventors further found that reduced coenzyme $Q_{10}$ may be obtained as a oily product with low viscosity, which is easy to handle, by heating reduced coenzyme $Q_{10}$ to the melting temperature or higher (or the temperature to start melting or higher, when the melting temperature is broad due to a solvent or impurities contained in reduced coenzyme $Q_{10}$), thereby completed the present invention useful for the production on the commercial scale.

Thus, the present invention is a method for producing reduced coenzyme $Q_{10}$ which comprises reacting oily oxidized coenzyme $Q_{10}$ with a reducing agent in water to synthesize oily reduced coenzyme $Q_{10}$.

According to the producing method of the present invention, oily reduced coenzyme $Q_{10}$ may be obtained by separating an aqueous phase from the obtained reaction mixture, and also its crystal may be obtained by cooling the obtained reaction mixture to crystallize reduced coenzyme $Q_{10}$ in the reaction system.

By the present invention, it becomes possible to generate reduced coenzyme $Q_{10}$ in a reaction system under a reduced atmosphere protected from oxidization, and further to transfer it to a crystalline state in said reaction system without requiring additional operations such as extraction of reduced coenzyme $Q_{10}$ into the organic phase, a complicated solvent substitution, etc., while dramatically decreasing the operation time. And the high-quality reduced coenzyme $Q_{10}$ crystal may be produced efficiently while minimizing formation of by-product oxidized coenzyme $Q_{10}$ in a sequence of processes from the reduction reaction of reduced coenzyme $Q_{10}$ to collecting of reduced coenzyme $Q_{10}$.

Moreover, the present invention is a method for obtaining reduced coenzyme $Q_{10}$ which comprises obtaining oily reduced coenzyme $Q_{10}$ from an organic phase containing reduced coenzyme $Q_{10}$ by distilling off an organic solvent at or above the melting temperature of reduced coenzyme $Q_{10}$.

According to the method of the present invention, oily reduced coenzyme $Q_{10}$ may be obtained from the organic phase containing reduced coenzyme $Q_{10}$ by distilling off an organic solvent in a convenient manner and in a short time, without causing stirring failure.

Additionally, oily reduced coenzyme $Q_{10}$ obtained by one of the above-mentioned methods may be made to a solution or slurry containing reduced coenzyme $Q_{10}$ in a simple manner by adding a desired solvent. Furthermore, reduced coenzyme $Q_{10}$ may be rapidly solidified and also obtained as a crystal by contacting a seed crystal of reduced coenzyme $Q_{10}$ to the obtained oily reduced coenzyme $Q_{10}$ at a temperature below the melting temperature of said oily product.

As described above, by the method of the present invention, not only additional operations such as extraction into the organic phase of reduced coenzyme $Q_{10}$ etc. are not necessary, but also in the cases where the organic phase containing reduced coenzyme $Q_{10}$ is concentrated, the high-quality reduced coenzyme $Q_{10}$ may be efficiently obtained while dramatically decreasing operation time and minimizing formation of by-product oxidized coenzyme $Q_{10}$ in a sequence of processes through the collection of reduced coenzyme $Q_{10}$ without causing problems such as increase of a stirring load or stirring failure.

Moreover, by the present invention, reduced coenzyme $Q_{10}$ may be easily obtained as a solution or slurry of the desired solvent, and it becomes possible to carry out the solvent substitution quite efficiently even in the cases of substituting solvents having a large difference in boiling points (namely, substitution from a high-boiling point solvent to a low-boiling point solvent), or the case solvents to be used each other form an azeotrope.

DETAILED DESCRIPTION OF THE INVENTION

In the following, the present invention is described in detail.

The present invention is intended for producing or obtaining oily reduced coenzyme $Q_{10}$ in order to shorten the process time of concentration, solvent substitution, etc. in view of favorably protecting reduced coenzyme $Q_{10}$ from oxidization. The present invention includes the following two aspects.

The first aspect is an invention for producing and obtaining oily reduced coenzyme $Q_{10}$ by reacting oily oxidized coenzyme $Q_{10}$ with a reducing agent in water, and the second aspect is an invention for producing or obtaining oily reduced coenzyme $Q_{10}$ by distilling off an organic solvent from the organic phase containing reduced coenzyme $Q_{10}$ at or above the melting temperature of reduced coenzyme $Q_{10}$.

First of all, the first aspect of the invention for obtaining oily reduced coenzyme $Q_{10}$ by reacting oily oxidized coenzyme $Q_{10}$ with a reducing agent in water is described.

In the present invention, reduced coenzyme $Q_{10}$ is synthesized by reacting oxidized coenzyme $Q_{10}$ with a reducing agent in water.

Oxidized coenzyme $Q_{10}$ used in the present invention may be a product comprising oxidized coenzyme $Q_{10}$ alone as the existing high-purity coenzyme $Q_{10}$ or may be a mixture comprising oxidized coenzyme $Q_{10}$ and reduced coenzyme $Q_{10}$.

Oily oxidized coenzyme $Q_{10}$ used in the present invention is obtained by melting oxidized coenzyme $Q_{10}$ to be oily form, and may contain various impurities and solvents in such amount that no adverse effect are occurred on a reaction. However, it is different from a solution which merely dissolves oxidized coenzyme $Q_{10}$ in an organic solvent.

The reaction solvent used in the present invention substantially consists of water alone. Although it may contain a small amount of an organic solvent, its content is preferably 10 w/w % or less, more preferably 5 w/w % or less, and still more preferably 1 w/w % or less relative to water.

The reducing agent to be used in the reduction reaction of oxidized coenzyme $Q_{10}$ is not particularly restricted, but is preferably iron (iron as a metal or salt), zinc (zinc as a metal) and dithionous acid or a salt thereof.

The reduction using iron or zinc is preferably carried out using an acid. The acid is not particularly restricted but includes, among others, fatty acids such as acetic acid, sulfonic acids such as methanesulfonic acid, and inorganic acids such as hydrochloric acid and sulfuric acid. Inorganic acids are preferred, and sulfuric acid is more preferred.

The amount of iron to be used is not particularly restricted but, for example, an amount of about ⅕ by weight or larger based on the charged weight of oxidized coenzyme $Q_{10}$ is appropriate for carrying out the reaction. The upper limit is not particularly restricted but, from the economical viewpoint, it is about twice the weight of the above charged weight. Iron may be used not only in the form of metallic iron but also in the form of a salt, for example iron(II) sulfate, etc.

The amount of zinc to be used is not particularly restricted but, for example, an amount of about 1/10 by weight or larger based on the charged weight of oxidized coenzyme $Q_{10}$ is appropriate for carrying out the reaction. The upper limit is not particularly restricted but, from the economic viewpoint, it is about twice the weight of the above charged weight.

The dithionous acid or a salt thereof is not particularly restricted but a salt form of dithionous acid is generally used. The salt of dithionous acid is not particularly restricted but includes, as preferred species, alkali metal salts, alkaline earth metal salts, ammonium salt and the like. Alkali metal salts such as the lithium salt, sodium salt, and potassium salt are more preferred, and the sodium salt is still more preferred.

The amount to be used of the dithionous acid or salt is not particularly restricted but it is not smaller than about ⅕ by weight, preferably not smaller than about ⅖ by weight, and more preferably not smaller than about ⅗ by weight, based on the charged weight of oxidized coenzyme $Q_{10}$. Larger amounts may be used without causing any particular trouble, but since such use is economically disadvantageous, the amount to be employed is preferably not larger than about twice the weight of the above-mentioned charged weight, more preferably not larger than the charged weight. Generally, the reaction can be more favorably carried out with employing an amount within the range of about ⅖ by weight of the above-mentioned charge to a weight roughly equal to that of the charged weight.

Among the above reducing agents, zinc and dithionous acid or a salt thereof are preferred, and dithionous acid or a salt thereof (specifically dithionous acid) are particularly preferred in view of the reduction ability, yield and quality.

The reduction using the above dithionous acid or a salt thereof is preferably carried out at pH of 7 or lower, more preferably at pH of 3 to 7, and still more preferably at pH of 3 to 6. The above pH may be adjusted by using an acid (e.g. mineral acids such as hydrochloric acid and sulfuric acid) or base (e.g. alkaline metal hydroxides such as sodium hydroxide).

The charging concentration of oxidized coenzyme $Q_{10}$ in the present invention is not particularly restricted, but the upper limit is preferably 30 w/w %, and more preferably 20 w/w % relative to water. The lower limit is preferably 1 w/w %, more preferably 5 w/w %, and still more preferably 10 w/w % in view of the productivity, etc.

When the generated reduced coenzyme $Q_{10}$ is crystallized from said reaction system after the above reduction reaction, the concentration of reduced coenzyme $Q_{10}$ may be appropriately increased or decreased for adjusting/maintaining the slurry concentration and slurry properties of the crystallized reduced coenzyme $Q_{10}$ within a preferable range. The weight of reduced coenzyme $Q_{10}$ after the reaction is preferably 20 w/w % or less and more preferably 15 w/w % or less relative to water in view of the slurry concentration and slurry properties.

The temperature for the reduction reaction in the present invention depends on the purity of oxidized coenzyme $Q_{10}$ or the ratio of oxidized coenzyme $Q_{10}$ and reduced coenzyme $Q_{10}$ thus cannot be absolutely specified. It is generally 45° C. or higher, preferably 48° C. or higher and more preferably 50° C. or higher. The upper limit is preferably the boiling point of the system, more preferably 100° C., still more preferably 80° C., and particularly preferably 60° C.

In the practice of the invention, the reduction reaction is preferably carried out under forced flowing. The power required for stirring to cause such flowing per unit volume is generally not less than about 0.01 kW/m³, preferably not less than about 0.1 kW/m³, and more preferably not less than about 0.3 kW/m³. The above forced flowing is generally caused by the turning of a stirring blade(s). The use of a stirring blade(s) is not always necessary if the above flowing can be otherwise obtained. For example a method based on liquid circulation may be utilized.

The above reduction reaction can be generally driven to completion within 48 hours, preferably within 24 hours, more preferably within 10 hours, and still more preferably within 5 hours.

In the above reduction reaction, especially in the reduction reaction using dithionous acid or a salt thereof, it is exceedingly preferable to carry out in a deoxygenated atmosphere. It was found that such atmosphere greatly contributes to an improvement in reduction reaction yield and a reduction in reducing agent amount. The deoxygenated atmosphere can be attained by substitution with an inert gas, pressure reduction, boiling, or a combination of these. It is preferable to carry out at least the substitution with an inert gas, namely to use an inert gas atmosphere. As the inert gas, there may be mentioned, for example, nitrogen gas, helium gas, argon gas, hydrogen gas, and carbon dioxide gas. Nitrogen gas is preferred, however.

Oily reduced coenzyme $Q_{10}$ may be obtained by separating an aqueous phase successively from the thus obtained reaction mixture, and if necessary, further by washing with water or brine, etc., for example. It is also possible to crystallize the generated reduced coenzyme $Q_{10}$ by cooling the above reaction mixture in said reaction system.

When reduced coenzyme $Q_{10}$ is obtained as an oily product, the separation of oily product and aqueous phase and, if needed, washing of the oily product are preferably carried out under warmed condition. The temperature depends on the purity, etc. of reduced coenzyme $Q_{10}$ and is not particularly restricted, but preferably about 45° C. or higher, more preferably about 48° C. or higher, and still more preferably about 50° C. or higher. The upper limit is preferably a boiling point of the system, more preferably about 100° C., still more preferably about 80° C. and particularly preferably about 60° C.

Moreover, reduced coenzyme $Q_{10}$ may also be obtained as a crystal by cooling the reaction mixture under reducing atmosphere. The cooling temperature is not particularly restricted, but preferably below about 50° C., more preferably below 48° C., and still more preferably below 45° C. The lower limit is a solidifying temperature of the system and more preferably 0° C. Generally, the cooling is preferably carried out at a temperature range of 0 to 40° C.

The cooling method for crystallization is not particularly restricted, but the cooling is preferably carried out at about 40° C./hour or less, more preferably at about 30° C./hour or less, and still more preferably at about 20° C./hour or less. Usually, filterability, slurry properties, etc. in the crystallization of reduced coenzyme $Q_{10}$ carried out in an organic solvent system is poor, thus the handling properties is not good in many cases. However, in a practice of the present invention, it is possible to obtain a crystal with large particle diameter, and these handling properties may be dramatically improved.

The crystallization of reduced coenzyme $Q_{10}$ is preferably carried out under forced flowing. The flowing is generally brought about by a stirring power per unit volume of not weaker than about 0.01 kW/m³, preferably not weaker than about 0.1 kW/m3, and more preferably not weaker than about 0.3 kW/m³. The forced flowing is generally provided by the turning of a stirring blade(s). However, the use of a stirring blade(s) is not always necessary if the above flowing can be otherwise obtained. For example, it is possible to utilize a method based on liquid circulation.

As described above, crystallization from a reaction mixture gives high-quality reduced coenzyme $Q_{10}$ crystal while minimizing formation of by-product oxidized coenzyme $Q_{10}$.

Next, the second aspect of the invention for obtaining oily reduced coenzyme $Q_{10}$ from an organic phase containing reduced coenzyme $Q_{10}$ by distilling off an organic solvent at or above the melting temperature of reduced coenzyme $Q_{10}$ is described.

As mentioned above, reduced coenzyme $Q_{10}$ which may be used in the present invention may be obtained by the conventional methods such as synthesis, fermentation, or extraction from a natural product, for example. Preferably it may be obtained by reducing oxidized coenzymes $Q_{10}$ such as an existing highly pure coenzyme $Q_{10}$ or a mixture of oxidized coenzyme $Q_{10}$ and reduced coenzyme $Q_{10}$ by using a common reducing agent. Firstly, a method for reducing oxidized coenzyme $Q_{10}$ is described.

Reduced coenzyme $Q_{10}$ is oxidized with molecular oxygen, and thereby easily produces by-product oxidized reduced coenzyme $Q_{10}$. Therefore, it is preferable to use a solvent having high ability of protecting reduced coenzyme $Q_{10}$ from oxidization as a solvent for the reduction process. As such solvents, it is preferable to use at least one species selected from among hydrocarbons, fatty acid esters, ethers and nitriles, and hydrocarbons are most preferable.

The hydrocarbons are not particularly restricted, but there may be mentioned, for example, aliphatic hydrocarbons, aromatic hydrocarbons, halogenated hydrocarbons, etc. Preferred are aliphatic hydrocarbons and aromatic hydrocarbons, and particularly preferred are aliphatic hydrocarbons.

The aliphatic hydrocarbons are not particularly restricted, and may be cyclic or acyclic, or saturated or unsaturated. However, generally they contain 3 to 20 carbon atoms, and preferably 5 to 12 carbon atoms.

As specific examples, there may be mentioned, for example, propane, butane, isobutane, pentane, 2-methylbutane, cyclopentane, 2-pentene, hexane, 2-methylpentane, 2,2-dimethylbutane, 2,3-dimethylbutane, methylcyclopentane, cyclohexane, 1-hexene, cyclohexene, heptane, 2-methylhexane, 3-methylhexane, 2,3-dimethylpentane, 2,4-dimethylpentane, methylcyclohexane, 1-heptene, octane, 2,2,3-trimethylpentane, isooctane, ethylcyclohexane, 1-octene, nonane, 2,2,5-trimethylhexane, 1-nonene, decane, 1-decene, p-menthane, undecane, dodecane, etc.

Among them, saturated aliphatic hydrocarbons having 5 to 8 carbon atoms are more preferred, and preferably used are pentane, 2-methylbutane and cyclopentane, which have 5 carbon atoms (referred to as "pentanes"); hexane, 2-methylpentane, 2,2-dimethylbutane, 2,3-dimethylbutane, methylcyclopentane, cyclohexane, which have 6 carbon atoms (referred to as "hexanes"); heptane, 2-methylhexane, 3-methylhexane, 2,3-dimethylpentane, 2,4-dimethylpentane, methylcyclohexane, which have 7 carbon atoms (referred to as "heptanes"); octane, 2,2,3-trimethylpentane, isooctane, ethylcyclohexane, which have 8 carbon atoms (referred to as octanes); and a mixture of these. In particular, the above heptanes are particularly preferred since they have a tendency to show a very high protection effect against oxidization, and heptane is most preferred.

The aromatic hydrocarbons are not particularly restricted, but generally they contain 6 to 20 carbon atoms, preferably 6 to 12 carbon atoms, and particularly preferably 7 to 10 carbon atoms. As specific examples, there may be mentioned, for example, benzene, toluene, xylene, o-xylene, m-xylene, p-xylene, ethylbenzene, cumene, mesitylene, tetralin, butylbenzene, p-cymene, cyclohexylbenzene, diethylbenzene, pentylbenzene, dipentylbenzene, dodecylbenzene, styrene, etc. Preferred are toluene, xylene, o-xylene, m-xylene, p-xylene, ethylbenzene, cumene, mesitylene, tetralin, butylbenzene, p-cymene, cyclohexylbenzene, diethylbenzene and pentylbenzene. More preferred are toluene, xylene, o-xylene, m-xylene, p-xylene, cumene and tetralin, and most preferred is cumene.

The halogenated hydrocarbons are not particularly restricted, and may be cyclic or acyclic, or saturated or unsaturated. But generally, acyclic halogenated hydrocarbons are preferably used. Usually, preferred are chlorinated hydrocarbons and fluorinated hydrocarbons, and chlorinated hydrocarbons are particularly preferred. Preferably, ones containing 1 to 6 carbon atoms, more preferably 1 to 4 carbon atoms, and particularly preferably 1 to 2 carbon atoms are used.

As specific examples, for example, there may be mentioned dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachloroethane, 1,1-dichloroethylene, 1,2-dichloroethylene, trichloroethylene, tetrachloroethylene, 1,2-dichloropropane, 1,2,3-trichloropropane, chlorobenzene, 1,1,1,2-tetrafluoroethane, etc.

Preferred are dichloromethane, chloroform, carbon tetrachloride, 1,1-dichloroethane, 1,2-dichloroethane, 1,1,1-trichloroethane, 1,1,2-trichloroethane, 1,1-dichloroethylene, 1,2-dichloroethylene, trichloroethylene, chlorobenzene and 1,1,1,2-tetrafluoroethane. More preferred are dichloromethane, chloroform, 1,2-dichloroethylene, trichloroethylene, chlorobenzene and 1,1,1,2-tetrafluoroethane.

The fatty acid esters are not particularly restricted, but there may be mentioned, for example, propionates, acetates, formates, etc. Particularly preferred are acetates and formates, and most preferred are acetates. Generally, ester functional groups thereof are not particularly restricted, but there may be mentioned alkyl or aralkyl group having 1 to 8 carbon atoms, preferably alkyl group having 1 to 6 carbon atoms, and more preferably alkyl group having 1 to 4 carbon atoms.

As the propionates, there may be mentioned, for example, methyl propionate, ethyl propionate, butyl propionate, and isopentyl propionate.

As the acetates, there may be mentioned, for example, methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate, benzyl acetate, etc. Preferred are methyl acetate, ethyl acetate, propyl acetate, isopropyl acetate, butyl acetate, isobutyl acetate, sec-butyl acetate, pentyl acetate, isopentyl acetate, sec-hexyl acetate and cyclohexyl acetate. More preferred are methyl acetate, ethyl acetate, propyl acetate, isopropyl acetate, butyl acetate and isobutyl acetate. Most preferred is ethyl acetate.

As the formates, there may be mentioned, for example, methyl formate, ethyl formate, propyl formate, isopropyl formate, butyl formate, isobutyl formate, sec-butyl formate, pentyl formate, etc. Preferred are methyl formate, ethyl formate, propyl formate, butyl formate, isobutyl formate and pentyl formate, and most preferred is ethyl formate.

The ethers are not particularly restricted, and may be cyclic or acyclic, or saturated or unsaturated. But generally, saturated ones are preferably used. Usually, ones containing 3 to 20 carbon atoms, and preferably 4 to 12 carbon atoms and particularly preferably 4 to 8 carbon atoms are used.

As specific examples, there may be mentioned, for example, diethyl ether, methyl tert-butyl ether, dipropyl ether, diisopropyl ether, dibutyl ether, dihexyl ether, ethyl vinyl ether, butyl vinyl ether, anisol, phenetole, butyl phenyl ether, methoxytoluene, dioxane, furan, 2-methylfuran, tetrahydrofuran, tetrahydropyran, ethylene glycol dimethyl ether, ethylene glycol diethyl ether, ethylene glycol dibutyl ether, ethylene glycol monomethyl ether, ethylene glycol monoethyl ether, ethylene glycol monobutyl ether, etc.

Preferred are diethyl ether, methyl tert-butyl ether, dipropyl ether, diisopropyl ether, dibutyl ether, dihexyl ether, anisol, phenetole, butyl phenyl ether, methoxytoluene, dioxane, 2-methylfuran, tetrahydrofuran, tetrahydropyran, ethylene glycol dimethyl ether, ethylene glycol diethyl ether, ethylene glycol dibutyl ether, ethylene glycol monomethyl ether and ethylene glycol monoethyl ether. More preferred are diethyl ether, methyl tert-butyl ether, anisol, dioxane, tetrahydrofuran, ethylene glycol monomethyl ether and ethylene glycol monoethyl ether. More preferred are diethyl ether, methyl tert-butyl ether, anisol, etc., and most preferred is methyl tert-butyl ether.

The nitriles are not particularly restricted, and may be cyclic or acyclic, or saturated or unsaturated. But generally, saturated ones are preferably used. Usually, ones containing 2 to 20 carbon atoms, preferably 2 to 12 carbon atoms, and particularly preferably 2 to 8 carbon atoms are used. As specific examples, there may be mentioned, for example, acetonitrile, propiononitrile, malononitrile, butyronitrile, isobutyronitrile, succinonitrile, valeronitrile, glutaronitrile, hexanenitrile, heptylcyanide, octylcyanide, undecanenitrile, dodecanenitrile, tridecanenitrile, pentadecanenitrile, stearonitrile, chloroacetonitrile, bromoacetonitrile, chloropropiononitrile, bromopropiononitrile, methoxyacetonitrile, methyl cyanoacetate, ethyl cyanoacetate, tolunitrile, benzonitrile, chlorobenzonitrile, bromobenzonitrile, cyanobenzoic acid, nitrobenzonitrile, anisonitrile, phthalonitrile, bromotolunitrile, methyl cyanobenzoate, methoxybenzonitrile, acetylbenzonitrile, naphthonitrile, biphenylcarbonitrile, phenylpropiononitrile, phenylbutyronitrile, methylphenylacetonitrile, diphenylacetonitrile, naphthylacetonitrile, nitrophenylacetonitrile, chlorobenzylcyanide, cyclopropanecarbonitrile, cyclohexanecarbonitrile, cycloheptanecarbonitrile, phenylcyclohexanecarbonitrile, tolylcyclohexanecarbonitrile, etc.

Preferred are acetonitrile, propiononitrile, succinonitrile, butyronitrile, isobutyronitrile, valeronitrile, methyl cyanoacetate, ethyl cyanoacetate, benzonitrile, tolunitrile and chloropropiononitrile. More preferred are acetonitrile, propiononitrile, butyronitrile and isobutyronitrile, and most preferred is acetonitrile.

In selecting the solvent to be used from among the solvents mentioned above, such properties as boiling point and viscosity are preferably taken into consideration (for example, the solvent should have a boiling point which allows appropriate warming for increasing the solubility and facilitates a solvent removal from wet masses by drying and solvent recovery from crystallization filtrates (about 30 to 150° C. at 1 atm), a melting point such that solidification hardly occurs in handling at room temperature as well as upon cooling to room temperature or below (not higher than about 20° C., preferably not higher than about 10° C., still more preferably not higher than about 0° C.), and a low viscosity (not higher than about $_{10}$ cp at 20° C.)). From the industrial operation viewpoint, a solvent which is hardly volatile at ordinary temperature is generally preferred; for example, one having a boiling point of not lower than about 80° C. is preferred, and one having a boiling point of not lower than about 90° C. is particularly preferred.

Among the solvents mentioned above, a solvent having low miscibility with water is particularly preferably used as a solvent in the reduction reaction. The solvent in the reduction reaction promotes purifying and obtaining a reduced coenzyme $Q_{10}$ efficiently, by extracting the reducing agent to be described below and/or impurities from the reducing agent and removing the same.

Reduced coenzyme $Q_{10}$ when in a dissolved state, tends to become more resistant to oxidation as the concentration thereof increases. Reduced coenzyme $Q_{10}$ is highly soluble in the solvents mentioned above and, in this respect, too, the above solvents are suitable for the protection from oxidation. The concentration of reduced coenzyme $Q_{10}$ which is preferred from the viewpoint of protection thereof from oxidation may vary depending on the solvent species, among others, hence cannot be absolutely specified. Generally, however, the concentration of reduced coenzyme $Q_{10}$ in the above solvents is generally not lower than 1 w/w %, preferably not lower than 2 w/w %. The upper limit is not particularly restricted but, from the practical operability viewpoint, it is 400 w/w % or below, preferably 200 w/w % or below, more preferably 100 w/w % or below, and still more preferably 50 w/w % or below.

Thus, when such a solvent as mentioned above is used, it is possible to minimize the undesirable oxygen-involving side reaction through the whole process of the reduction reaction.

The reduction of oxidized coenzyme $Q_{10}$ is carried out using, as a solvent, a metal hydride compound, iron (metallic iron or iron in a salt form), zinc (metallic zinc), dithionous acid or a salt thereof, or an ascorbic acid or a related compound thereof in the above-mentioned solvent.

The metal hydride compound is not particularly restricted but includes, among others, sodium borohydride and lithium aluminum hydride. The amount to be used of the metal hydride compound may vary depending on the species thereof, hence cannot be absolutely specified. Generally, however, the reduction can be favorably carried out by using it in an amount of 1 to 3 times the theoretical hydrogen equivalent.

The reduction using iron or zinc is preferably carried out using an acid. The acid is not particularly restricted but includes, among others, fatty acids such as acetic acid, sulfonic acids such as methanesulfonic acid, and inorganic acids such as hydrochloric acid and sulfuric acid. Inorganic acids are preferred, and sulfuric acid is more preferred.

The amount of iron to be used is not particularly restricted but, for example, an amount of about ⅕ by weight or larger based on the charged weight of oxidized coenzyme $Q_{10}$ is appropriate for carrying out the reaction. The upper limit is not particularly restricted but, from the economical viewpoint, it is about twice the weight of the above charged weight or lower. Iron may be used not only in the form of metallic iron but also in the form of a salt, for example iron(II) sulfate, etc.

The amount of zinc to be used is not particularly restricted but, for example, an amount of about ¹⁄₁₀ by weight or larger based on the charged weight of oxidized coenzyme $Q_{10}$ is appropriate for carrying out the reaction. The upper limit is not particularly restricted but, from the economic viewpoint, it is about twice the weight of the above charged weight or lower.

The dithionous acid or a salt thereof is not particularly restricted but a salt form of dithionous acid is generally used. The salt of dithionous acid is not particularly restricted but includes, as preferred species, alkali metal salts, alkaline earth metal salts, ammonium salt and the like. Alkali metal salts such as the lithium salt, sodium salt, and potassium salt are more preferred, and the sodium salt is still more preferred.

The amount to be used of the dithionous acid or salt is not particularly restricted but it is preferably not smaller than about ⅕ by weight, more preferably not smaller than about ⅖ by weight, and still more preferably not smaller than about ⅗ by weight, based on the charged weight of oxidized coenzyme $Q_{10}$. Larger amounts may be used without causing any particular trouble, but since such use is economically disadvantageous. Thus, the amount to be employed is preferably not larger than about twice the weight of the above-mentioned charged weight, more preferably not larger than the charged weight. Generally, the reaction can be favorably carried out with employing an amount within the range of about ⅖ by weight of the above-mentioned charge to a weight roughly equal to that of the charged weight.

The ascorbic acid or related compounds thereof are not particularly restricted, and include, for example, not only ascorbic acid, but also rhamno-ascorbic acid, arabo-ascorbic acid, gluco-ascorbic acid, fuco-ascorbic acid, glucohepto-ascorbic acid, xylo-ascorbic acid, galacto-ascorbic acid, gulo-ascorbic acid, allo-ascorbic acid, erythro-ascorbic acid, 6-desoxyascorbic acid, and the like ascorbic acid related compounds, and may be ester forms or salts of these. Furthermore, these may be L-form, D-form or racemic form. Specifically, there may be mentioned, for example, L-ascorbic acid, L-ascorbyl palmitate, L-ascorbyl stearate, D-arabo-ascorbic acid, etc. In producing the reduced coenzyme $Q_{10}$ any of the above-mentioned ascorbic acid and related compounds thereof may be suitably used. However, the water-soluble ones are suitably used in particular among the above-mentioned ascorbic acid or related compounds thereof in view of separatability with the generated reduced coenzyme $Q_{10}$ etc. And most preferred is a free form of L-ascorbic acid, D-arabo-ascorbic acid, and the like in view of the ready availability, price, etc.

The amount to be used of the ascorbic acid or a related compound thereof mentioned above is not particularly restricted but may be an amount effective in converting oxidized coenzyme $Q_{10}$ to reduced coenzyme $Q_{10}$. It is preferably not smaller than 1 mole, more preferably not smaller than 1.2 moles, per mole of oxidized coenzyme $Q_{10}$. The upper limit is not particularly restricted but, from the economical viewpoint, it is preferably 10 moles, more preferably 5 moles, and still more preferably 3 moles, per mole of the oxidized coenzyme $Q_{10}$.

Among the reducing agent species mentioned above, zinc, dithionous acid and salts thereof, and ascorbic acid and related compounds thereof are preferred from the viewpoint of reducing ability, yield and/or quality, among others, and, in particular, dithionous acid or salts thereof (specifically dithionous acid salts) and ascorbic acid or related compounds thereof are preferred.

In carrying out the reduction reaction, an alcohol and/or water are/is suitably used singly or in combination, as mentioned below. Water is preferred in particular when iron, zinc, or dithionous acid or a salt thereof is used as the reducing agent. When a metal hydride compound or an ascorbic acid or a related compound thereof is used as the reducing agent, an alcohol can be used in combination. The combined use of water and an alcohol exhibits the characteristics of both water and the alcohol and contributes to improvements in reaction rate and yield, among others.

In the following, a preferred method of reduction is described in detail.

The reduction using dithionous acid or a salt thereof is preferably carried out in a mixed solvent system composed of water and at least one organic solvent selected from among the above-mentioned hydrocarbons, fatty acid esters, ethers, and nitriles (preferably hydrocarbons, more preferably aliphatic hydrocarbons, and among them, still more preferably heptanes and particularly preferably heptane). On that occasion, the reaction is preferably carried out preferably at pH of not higher than 7, more preferably at pH 3 to 7, still more preferably at pH 3 to 6, from the viewpoint of yield, etc. The pH can be adjusted using an acid (e.g. an inorganic acid such as hydrochloric acid or sulfuric acid) or a base (e.g. an alkali metal hydroxide such as sodium hydroxide).

In the reduction using dithionous acid or a salt thereof, the amount of water is not particularly restricted but may be an amount of water such that an appropriate amount of the reducing agent, namely dithionous acid or a salt thereof, can be dissolved therein. Thus, it is preferable that the amount of the dithionous acid or a salt be adjusted preferably to not more than 30 w/w %, and more preferably not more than 20 w/w %, relative to the weight of water. From the productivity viewpoint, among others, it is advisable that the amount be adjusted preferably to not less than 1 w/w %, more preferably not less than 5 w/w %, and still more preferably not less than 10 w/w %.

The reduction using the ascorbic acid or a related compound thereof mentioned above may be preferably carried out using a solvent especially highly miscible with water as selected from among the above-mentioned hydrocarbons, fatty acid esters, ethers, and nitrites, in particular ethers and nitriles, which are highly miscible with water, and more specifically tetrahydrofuran, dioxane, acetonitrile or the like.

Furthermore, it is particularly preferable to use the alcohols and/or ketones mentioned below (preferably alcohols and/or ketones having high miscibility with water (specifically, as an alcohol, a monohydric or a dihydric (preferably monohydric) alcohol containing 1 to 5 carbon atoms, preferably containing 1 to 4 carbon atoms, and more preferably containing 1 to 3 carbon atoms, and as a ketone, acetone, methyl ethyl ketone, etc.)). Namely, in the reduction using the ascorbic acid or a related compound thereof, it is preferable to use alcohols and/or water-soluble organic solvents. Furthermore, from the viewpoint of reaction promotion (e.g. reaction temperature lowering or reaction time shortening) in the production of reduced coenzyme $Q_{10}$ it is also possible to carry out the reduction in the presence of an additive having a reaction promoting effect, such as a basic substance or a hydrogensulfite.

The basic compound is not particularly restricted but may be either an inorganic compound or an organic compound. The inorganic compound is not particularly restricted but includes, among others, hydroxides, carbonates, and hydrogencarbonates of metals (preferably alkali metals, alkaline earth metals, and the like), and ammonia. As typical examples thereof, there may be mentioned alkali metal hydroxides such as sodium hydroxide, alkali metal carbonates such as sodium carbonate, alkali metal hydrogencarbonates such as sodium hydrogencarbonate, and alkaline earth metal carbonates such as magnesium carbonate. The organic compound is not particularly restricted but includes, among others, amines such as triethylamine. Among the basic substances specifically mentioned above, weakly basic substances (weak bases or weak alkalis) such as the carbonates and hydrogencarbonates of metals (preferably alkali metals, alkaline earth metals, etc.), ammonia, and like inorganic compounds; amines such as triethylamine, and like organic compounds are preferably used. More preferred are the weakly basic inorganic compounds mentioned above.

Preferred as the hydrogensulfite are, for example, alkali metal hydrogensulfites such as sodium hydrogensulfite, etc.

The amount of the additive mentioned above is not particularly restricted but may be such that the reaction promoting effect of the additive can be produced to a desired extent (effective amount). But generally, from the economical viewpoint, the amount is preferably not more than 20 moles, more preferably not more than 10 moles, still more preferably not more than 5 moles, and particularly preferably not more than 2 moles, per mole of the ascorbic acid or a related compound thereof. The lower limit is not particularly restricted but, preferably, it is 0.01 moles, more preferably 0.05 moles, still more preferably 0.1 moles, and particularly preferably 0.2 moles, per mole of the ascorbic acid or a related compound thereof.

The reduction reaction is preferably carried out under forced flowing. The power required for stirring to cause such flowing per unit volume is preferably not less than about 0.01 $kW/m^3$, more preferably not less than about 0.1 $kW/m^3$, and still more preferably not less than about 0.3 $kW/m^3$. The above forced flowing is generally caused by the turning of a stirring blade(s). The use of a stirring blade(s) is not always necessary if the above flowing can be otherwise obtained. For example a method based on liquid circulation may be utilized.

The reduction temperature may vary depending on the reducing agent species and/or amount, hence cannot be absolutely specified. In the reduction using dithionous acid or a salt thereof, for instance, the reduction is preferably carried out at 100° C. or below, more preferably at 80° C. or below, still more preferably at 60° C. or below. The lower limit is preferably the solidification temperature of the system. Thus, the reduction can be favorably carried out generally at about 0 to 100° C., preferably at about 0 to 80° C., more preferably at about 0 to 60° C. In the reduction using an ascorbic acid or a related compound thereof, the reduction is carried out preferably at 30° C. or higher, more preferably at 40° C. or higher, still more preferably at 50° C. or higher. The upper limit is preferably the boiling point of the system. Thus, the reduction can be favorably carried out generally at about 30 to 150° C., preferably about 40 to 120° C., and more preferably at about 50 to 100° C.

Generally, the reaction concentration is not particularly restricted but the weight of oxidized coenzyme $Q_{10}$ relative to the solvent weight is preferably not less than about 1 w/w %, more preferably not less than 3 w/w %, still more preferably not less than 10 w/w %, and particularly preferably not less than 15 w/w %. The upper limit is not particularly restricted but is preferably not higher than about 60 w/w %, more preferably not higher than 50 w/w %, still more preferably not higher than 40 w/w %, and particularly preferably not higher than 30 w/w %. Generally, the reaction can be favorably carried out at a reaction concentration of about 1 to 60 w/w %, preferably about 3 to 50 w/w %, and more preferably about 10 to 40 w/w %.

The reduction reaction can be driven to completion generally within 48 hours, preferably within 24 hours, more preferably within $_{10}$ hours, and still more preferably within 5 hours.

An organic phase containing the product reduced coenzyme $Q_{10}$ is recovered from the thus-obtained reduction reaction mixture and, if necessary (preferably), the organic phase is further washed repeatedly using water, brine or the like to achieve complete contaminant elimination.

It is exceedingly preferable to carry out the above-mentioned reduction reaction and post-treatments in a deoxygenated atmosphere. Surprisingly, it was found that, particularly in the reduction reaction using dithionous acid or a salt thereof, such atmosphere greatly contributes to an improvement in reduction reaction yield and a reduction in reducing agent amount. The deoxygenated atmosphere can be attained by substitution with an inert gas, pressure reduction, boiling, or a combination of these. It is preferable to carry out at least the substitution with an inert gas, namely to use an inert gas atmosphere. As the inert gas, there may be mentioned, for example, nitrogen gas, helium gas, argon gas, hydrogen gas, and carbon dioxide gas. Nitrogen gas is preferred, however.

Secondly, a method for obtaining oily product, a solution and slurry of reduced coenzyme $Q_{10}$ from the organic phase containing the thus obtained reduced coenzyme $Q_{10}$ is described.

The organic phase containing reduced coenzyme $Q_{10}$ used for obtaining oily reduced coenzyme $Q_{10}$ is not particularly restricted, but it is preferably an organic solvent having high ability of protecting reduced coenzyme $Q_{10}$ from oxidization for obtaining the high-quality reduced coenzyme $Q_{10}$ while inhibiting an undesirable side reaction caused by oxygen. Namely, a solution comprising at least one species selected from among hydrocarbons, fatty acid esters, ethers and nitrites is preferred. Among them, as an organic solvent, hydrocarbons and fatty acid esters are preferred, and hydrocarbons are more preferred, and heptanes are most preferred. The organic phase containing reduced coenzyme $Q_{10}$ used in the present invention may be either the above solution or a condensate obtained by concentrating said solution by a common method.

In the present invention, an organic solvent is distilled off at or above the melting temperature of reduced coenzyme $Q_{10}$ in concentrating the organic phase containing reduced coenzyme $Q_{10}$ to remove the coexisting solvent completely or almost completely. Thus, oily reduced coenzyme $Q_{10}$ is obtained. When the melting temperature is broad due to a solvent or impurities contained in reduced coenzyme $Q_{10}$ the temperature for obtaining oily reduced coenzyme $Q_{10}$ may be a temperature to start melting, or higher.

In the present invention, the above temperature for obtaining oily reduced coenzyme $Q_{10}$ depends on the amount of the coexisting organic solvent, and thus cannot be absolutely specified. But it is preferably 40° C. or more, more preferably 45° C. or more, still more preferably 50° C. or more and particularly preferably 60° C. or more. Although it depends on the species and amount of the solvent, the solvent may be preferably removed at a temperature range of 40 to 140° C., more preferably 40 to 100° C. and still more preferably 50 to 80° C. The above concentration is carried out under normal pressure or reduced pressure.

By the above method, reduced coenzyme $Q_{10}$ may be preferably obtained as oily product while completely distilling off the organic solvent without causing stirring failure, even in the cases that the purity of reduced coenzyme $Q_{10}$ in the organic phase is preferably about 80% by weight or more, more preferably about 90% by weight or more, and still more preferably about 95% by weight or more. The above purity may be obtained by HPLC as described below.

Regarding an aspect for obtaining oily reduced coenzyme $Q_{10}$ by removing a solvent, the content of the solvent in above-mentioned oily reduced coenzyme $Q_{10}$ is preferably 10% by weight or less, more preferably 5% by weight or less, and still more preferably 2% by weight or less.

As described above, oily reduced coenzyme $Q_{10}$ may be obtained quite conveniently and efficiently by using the above two species of aspects.

Moreover, oily reduced coenzyme $Q_{10}$ obtained by the above aspects is favorably protected from oxidization by adding a desired solvent so that reduced coenzyme $Q_{10}$ should not become oxidized coenzyme $Q_{10}$ and thus may be made to a solution or slurry of the high-quality reduced coenzyme $Q_{10}$ quite efficiently.

Particularly, when the organic solvent containing reduced coenzyme $Q_{10}$ is substituted with another solvent, the effect of the present invention may be performed to the utmost extent by using either one of the aspects described below or a combination of two or more aspects described below.

The first aspect is an aspect in which the solvent added for obtaining a solution or slurry of reduced coenzyme $Q_{10}$ has a lower boiling point than that of the organic solvent to be distilled off. Usually, the substitution of a solvent having a high-boiling point with a solvent having a low-boiling point is inefficient, but it becomes possible to be carried out the substitution efficiently by the present invention. For example, there may be mentioned substitutions of heptane with acetone, toluene with ethanol, ethyl acetate with diethyl ether and heptane with ethanol, and the like.

The second aspect is an aspect in which the solvent added for obtaining a solution or slurry of reduced coenzyme $Q_{10}$ forms an azeotrope with the organic solvent to be distilled off. Usually, the solvent substitution is inefficient by a formation and/or removal of an azeotrope, but it becomes possible to be carried out efficiently by the present invention. For example, there may be mentioned substitutions of heptane with ethanol, chloroform with acetone and ethyl acetate with ethanol.

The third aspect is an aspect in which the solvent added for obtaining a solution or slurry of reduced coenzyme $Q_{10}$ contains a hardly volatile component. The "hardly volatile component" means a component which is hardly distilled off in a usual condition of solvent distillation and solvent substitution, and for example, there may be mentioned 2,6-di-tert-butyl-4-hydroxytoluene (BHT) contained in ether as a stabilizer, and the like. In an inefficient solvent substitution comprising repeated supplements and removals of a solvent, a hardly volatile component tends to accumulate in high concentration in the solution. For example, when a solvent substitution of heptane with tetrahydrofuran is inefficient, the above BHT can accumulate in high concentration more than necessary. However, by the present invention, the solvent substitution may be preferably carried out while inhibiting accumulation of a hardly volatile component.

The fourth aspect is an aspect in which the solvent added for obtaining a solution or slurry of reduced coenzyme $Q_{10}$ has a less ability to protect reduced coenzyme $Q_{10}$ from oxidization than the organic solvent to be distilled off. In an inefficient solvent substitution, undesirable side reaction by oxygen tends to occur while the solvent substitution over long period of time is carried out under coexistence of a solvent, which does not have very high protection effect from oxidization. However, by the present invention, the solvent substitution may be preferably carried out while inhibiting the undesirable side reaction by oxygen by minimizing contact time with the solvent which does not have very high protection effect from oxidization. For example, there may be mentioned substitutions of heptane with methyl isobutyl ketone and xylene with dimethylformamide, and the like.

The solvent added for obtaining a solution or slurry of reduced coenzyme $Q_{10}$ is not particularly restricted, but preferably at least one species selected from among hydrocarbons, fatty acid esters, ethers and nitriles mentioned above, and also water, alcohols, fatty acids, ketones, nitrogen-containing compounds (except for nitriles), sulfur-containing compounds, etc. More preferably, it is at least one species selected from among alcohols, nitriles, ketones, ethers and water. And particularly preferred are alcohols and/or ketones since the slurry or crystalline properties becomes better.

The alcohols are not particularly restricted but may be cyclic or acyclic, or saturated or unsaturated. Saturated ones are preferred, however. Generally, they contain 1 to 20 carbon atoms, preferably 1 to 12 carbon atoms, more preferably 1 to 6 carbon atoms, and still more preferably 1 to 5 carbon atoms. Furthermore, dihydric alcohols containing 2 to 5 carbon atoms, and the trihydric alcohol containing 3 carbon atoms are preferred, among others.

The monohydric alcohol is not particularly restricted, and there may be mentioned, for example, methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, allyl alcohol, propargyl alcohol, benzyl alcohol, cyclohexanol, 1-methylcyclohexanol, 2-methylcyclohexanol, 3-methylcyclohexanol, 4-methylcyclohexanol, etc.

Preferred are methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol and cyclohexanol. More preferred are methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol and neopentyl alcohol. Still more preferred are methanol, ethanol, 1-propanol, 2-propanol, 1-butanol, 2-butanol, isobutyl alcohol, 2-methyl-1-butanol and isopentyl alcohol. Most preferred is ethanol.

The dihydric alcohol is not particularly restricted, and there may be mentioned, for example, 1,2-ethanediol, 1,2-propandiol, 1,3-propandiol, 1,2-butanediol, 1,3-butanediol, 1,4-butanediol, 2,3-butanediol, 1,5-pentanediol, etc. Preferred are 1,2-ethanediol, 1,2-propandiol and 1,3-propandiol, and most preferred is 1,2-ethanediol.

The trihydric alcohol is not particularly restricted, and glycerol, etc. may be preferably used, for example.

The ketones are not particularly restricted, and ones having 3 to 6 carbon atoms are preferably used. As specific examples, there may be mentioned, for example, acetone, methyl ethyl ketone, methyl butyl ketone, methyl isobutyl ketone, etc. Preferred are acetone and methyl ethyl ketone, and most preferred is acetone.

In a sequence of investigations according to the present invention, there is a possibility in a commercial scale production that reduced coenzyme $Q_{10}$ melts during a drying process of crystals or long period of time is required for drying. Thus, it was found that it was not always easy to obtain reduced coenzyme $Q_{10}$ crystal. However, it was also found that the crystal might be rapidly and adequately solidified by contacting the above oily reduced coenzyme $Q_{10}$ with a seed crystal (reduced coenzyme $Q_{10}$ own crystal) at a temperature below the melting temperature of the oily product. Therefore, as an aspect further exerting the effect of the present invention, there may be mentioned a solidification method which comprises contacting a seed crystal of reduced coenzyme $Q_{10}$ at a temperature below the melting temperature of oily reduced coenzyme $Q_{10}$ to solidify it more rapidly and adequately. By this method, the solid of reduced coenzyme $Q_{10}$ may be preferably obtained in a high yield while preventing losses occurred in ordinary crystallizations by using organic solvent as well as preventing losses of agents and time.

In this case, a solid may be obtained by forming the above oily product into a desired form after decreasing the temperature of the oily product to below the melting temperature thereof and contacting with the seed crystal. The contact with the seed crystal may be performed either before or after said formation from the oily product. The solidifying temperature is not particularly restricted provided that it is below the melting temperature of the oily product, but generally below 48° C., preferably below 45° C., and more preferably below 40° C. It is desirably 0° C. or more.

The thus-obtained crystals of reduced coenzyme $Q_{10}$ as mentioned above can be preferably recovered as a wet product, for example, by such a solid-liquid separation technique as centrifugation, pressure filtration, or vacuum filtration, and followed by cake washing. They can be recovered also as a dry product by further charging the wet product in a reduced pressure drier (vacuum drier) internally purged with an inert gas and drying the same under reduced pressure. The recovery in a dry form is preferred.

When the present invention is practiced in a deoxygenated atmosphere, the protective effect against oxidation can be further increased. The deoxygenated atmosphere can be attained by inert gas substitution, pressure reduction, boiling, or a combination of these. It is preferable to carry out at least the substitution with an inert gas, namely to use an inert gas atmosphere. As the inert gas, there may be mentioned, for example, nitrogen gas, helium gas, argon gas, hydrogen gas, and carbon dioxide gas. Nitrogen gas is preferred, however.

BEST MODE FOR CARRYING OUT THE INVENTION

The following examples illustrate the present invention in further detail. These examples are, however, by no means limitative of the scope of the present invention. In the examples, the purity of reduced coenzyme $Q_{10}$ and the reduced coenzyme $Q_{10}$/oxidized coenzyme $Q_{10}$ weight ratio were determined by the HPLC analysis specified below. The reduced coenzyme $Q_{10}$ purity values as determined, however, are by no means indicative of the limit purity value attainable in accordance with the present invention. Likewise, the reduced coenzyme $Q_{10}$/oxidized coenzyme $Q_{10}$ weight ratio values obtained never indicate the upper limit to that ratio.

(HPLC Conditions)

Column: SYMMETRY C18 (product of Waters), 250 mm (in length), 4.6 mm (in inside diameter); mobile phase: $C_2H_5OH:CH_3OH=4:3$ (v/v); detection wavelength: 210 nm; flow rate: 1 ml/min; retention time of reduced coenzyme $Q_{10}$: 9.1 min; retention time of oxidized coenzyme $Q_{10}$: 13.3 min.

EXAMPLE 1

Oxidized coenzyme $Q_{10}$ (100 g; purity 99.4%) was melted at 50° C. with stirring. While stirring (power required for stirring: 0.3 kW/m³), an aqueous solution prepared by dissolving 100 g of sodium dithionite (purity: at least 75%), as the reducing agent, in 1000 ml of water was gradually added to this oily product and the reduction reaction was carried out at 50° C. and at pH 4 to 6. After the lapse of 2 hours, the mixture was cooled to 2° C. while stirring (power required for stirring: 0.3 kW/m³) to give white slurry. All the above operations were carried out in a nitrogen atmosphere. The slurry obtained was filtered under reduced pressure, and the wet crystals were washed in sequence with cold water and cold ethanol (the cold solvents used for washing having a temperature of 2° C.). The wet crystals were further dried under reduced pressure (20-40° C., 1-30 mmHg) to give 98 g of white dry crystals (isolated product yield: 98 mole percent). The reduced coenzyme $Q_{10}$/oxidized coenzyme $Q_{10}$ weight ratio of the crystals obtained was 99.5/0.5, and the purity of the reduced coenzyme $Q_{10}$ was 99.2%.

EXAMPLE 2

Oxidized coenzyme $Q_{10}$ (100 g; purity 99.4%) was melted at 50° C. with stirring. While stirring (power required for stirring: 0.3 kW/m3), an aqueous solution prepared by dissolving 100 g of sodium dithionite (purity: at least 75%), as the reducing agent, in 1000 ml of water was gradually added to this oily product and the reduction reaction was carried out at 50° C. and at pH 4 to 6. After the lapse of 2 hours, the aqueous phase containing the oily product was removed from the reaction mixture, and 1400 g of ethanol warmed to 50° C. was added. Then, the mixture was cooled to 2° C. while stirring (power required for stirring: 0.3 kW/m³) to give white slurry. All the above operations were carried out in a nitrogen atmosphere. The slurry obtained was filtered under reduced pressure, and the wet crystals were washed in sequence with cold ethanol, cold water and cold ethanol (the cold solvents used for washing having a temperature of 2° C.). The wet crystals were further dried under reduced pressure (20-40° C., 1-30 mmHg) to give 95 g of white dry crystals (isolated product yield: 95 mole percent). The reduced coenzyme $Q_{10}$/oxidized coenzyme $Q_{10}$ weight ratio of the crystals obtained was 99.4/0.6, and the purity of the reduced coenzyme $Q_{10}$ was 99.2%.

EXAMPLE 3

Oxidized coenzyme $Q_{10}$ (100 g, purity 99.4%) was melted at 50° C. with stirring. While stirring (power required for stirring: 0.3 kW/m³), an aqueous solution prepared by dissolving 100 g of sodium dithionite (purity: at least 75%), as the reducing agent, in 1000 ml of water was gradually added to this oily product and the reduction reaction was carried out at 50° C. and at pH 4 to 6. The aqueous phase was removed from the reaction mixture containing the oil product, and the oily product was washed 6 times with 1000 g of deaerated saturated brine heated to 50° C. to give oily reduced coenzyme $Q_{10}$. All the above operations were carried out in a nitrogen atmosphere. To this oily product, ethanol of 25° C. was added to give white slurry of reduced coenzyme $Q_{10}$. The slurry obtained was cooled to 2° C., filtered under reduced pressure, and the wet crystals were washed in sequence with cold ethanol, cold water and cold ethanol (the cold solvents used for washing having a temperature of 2° C.). The wet crystals were further dried under reduced pressure (20-40° C., 1-30 mmHg) to give 95 g of white dry crystals (isolated product yield: 95 mole percent). The reduced coenzyme $Q_{10}$/oxidized coenzyme $Q_{10}$ weight ratio of the crystals obtained was 99.4/0.6, and the purity of the reduced coenzyme $Q_{10}$ was 99.2%.

EXAMPLE 4

Oxidized coenzyme $Q_{10}$ (100 g) was melted at 48° C. with stirring. While stirring (power required for stirring: 0.3 kW/m³), an aqueous solution prepared by dissolving 100 g of sodium dithionite (purity: at least 75%), as the reducing agent, in 1000 ml of water was gradually added to this oily product and the reduction reaction was carried out at 50° C. and at pH 4 to 6. The aqueous phase was removed from the reaction mixture containing the oily product, and the oily product was washed 6 times with 1000 g of deaerated saturated brine heated to 48° C. to give oily reduced coenzyme $Q_{10}$. All the above operations were carried out in a nitrogen atmosphere. To this oil, toluene was added to prepare a toluene solution containing reduced coenzyme $Q_{10}$. The weight ratio of reduced coenzyme $Q_{10}$/oxidized coenzyme $Q_{10}$ in this toluene solution was 99.5/0.5.

EXAMPLE 5

Oily reduced coenzyme $Q_{10}$ obtained in Example 2 was dripped on a plate (40° C.) on which the reduced coenzyme $Q_{10}$ own crystal being spread, then the oily product was rapidly solidified, and a solid in the hemisphere shape was obtained.

COMPARATIVE EXAMPLE 1

Oily reduced coenzyme $Q_{10}$ obtained in Example 2 was dripped on a plate (40° C.) on which no reduced coenzyme $Q_{10}$ own crystal being spread, and the temperature was maintained for 1 hour, but no solidification occurred.

EXAMPLE 6

Oxidized coenzyme $Q_{10}$ (100 g) was melted at 50° C. While stirring (power required for stirring: 0.3 kW/m³), an aqueous solution prepared by dissolving 60 g of sodium dithionite (purity: at least 75%), as the reducing agent, in 1000 ml of water was gradually added to the obtained oily product and the reduction reaction was carried out at 50° C. and at pH 4 to 6. After the lapse of 2 hours, the aqueous phase containing oil was removed from the reaction mixture to give oily reduced coenzyme $Q_{10}$. The reduced coenzyme $Q_{10}$/oxidized coenzyme $Q_{10}$ weight ratio in the obtained oily product was 99.3/0.7. All the above operations were carried out in a nitrogen atmosphere.

EXAMPLE 7

Oxidized coenzyme $Q_{10}$ (100 g; purity 99.4%) was dissolved in 1000 g of heptane at 25° C. While stirring (power required for stirring: 0.3 kW/m$^3$), an aqueous solution prepared by dissolving 100 g of sodium dithionite (purity: at least 75%), as the reducing agent, in 1000 ml of water was gradually added and the reduction reaction was carried out at 25° C. and at pH 4 to 6. After the lapse of 2 hours, the aqueous phase was removed from the reaction mixture, and the heptane phase was washed 6 times with 1000 g of deaerated saturated brine. All the above operations were carried out in a nitrogen atmosphere. From this heptane solution, heptane was distilled off under reduced pressure at 50° C. to give oily reduced coenzyme $Q_{10}$. This oil was easily stirred and brushed away. The reduced coenzyme $Q_{10}$/oxidized coenzyme $Q_{10}$ weight ratio of the crystals of this oil was 99.5/0.5. The residual amount of heptane was 1.3%, and the purity of reduced coenzyme $Q_{10}$ was without heptane was 99.2%.

COMPARATIVE EXAMPLE 2

A heptane solution of reduced coenzyme $Q_{10}$ was obtained in the same manner as in Example 7. Heptane was distilled off from this heptane solution at 30° C. under reduced pressure. Reduced coenzyme $Q_{10}$ was adhered on a wall of the container, and was difficult to brush away.

EXAMPLE 8

A heptane solution of reduced coenzyme $Q_{10}$ was obtained in the same manner as in Example 7. Heptane was distilled off from this heptane solution at 48° C. under reduced pressure to obtain oily reduced coenzyme $Q_{10}$. 1000 g of tetrahydrofuran was added to give a tetrahydrofuran solution of reduced coenzyme $Q_{10}$. The reduced coenzyme $Q_{10}$/oxidized coenzyme $Q_{10}$ weight ratio in the solution was 99.5/0.5.

EXAMPLE 9

Oxidized coenzyme $Q_{10}$ (100 g; purity 99.4%) was dissolved in 1000 g of hexane at 25° C. While stirring (power required for stirring: 0.3 kW/m3), an aqueous solution prepared by dissolving 100 g of sodium dithionite (purity: at least 75%), as the reducing agent, in 1000 ml of water was gradually added and the reduction reaction was carried out at 25° C. and at pH 4 to 6. After the lapse of 2 hours, the aqueous phase was removed from the reaction mixture, and the hexane phase was washed 6 times with 1000 g of deaerated saturated brine. All the above operations were carried out in a nitrogen atmosphere. From this hexane solution, hexane was distilled off under reduced pressure at 50° C. to give oily reduced coenzyme $Q_{10}$. To this oily product, 1000 g of ethanol of 50° C. was added to give an ethanol solution of reduced coenzyme $Q_{10}$. The reduced coenzyme $Q_{10}$/oxidized coenzyme $Q_{10}$ weight ratio in the solution was 99.4/0.6.

EXAMPLE 10

Oxidized coenzyme $Q_{10}$ (100 g; purity 99.4%) was dissolved in 1000 g of hexane at 25° C. While stirring (power required for stirring: 0.3 kW/m$^3$), an aqueous solution prepared by dissolving 100 g of sodium dithionite (purity: at least 75%), as the reducing agent, in 1000 ml of water was gradually added and the reduction reaction was carried out at 25° C. and at pH 4 to 6. After the lapse of 2 hours, the aqueous phase was removed from the reaction mixture, and the hexane phase was washed 6 times with 1000 g of deaerated saturated brine. All the above operations were carried out in a nitrogen atmosphere. From this hexane solution, hexane was distilled off under reduced pressure at 50° C. to give oily reduced coenzyme $Q_{10}$. To this oily product, 1000 g of ethanol of 25° C. was slowly added to give white slurry of reduced coenzyme $Q_{10}$. The slurry obtained was cooled to 2° C., filtered under reduced pressure, and the wet crystals were washed in sequence with cold ethanol, cold water and cold ethanol (the cold solvents used for washing having a temperature of 2° C.). The wet crystals were further dried under reduced pressure (20-40° C., 1-30 mmHg) to give 95 g of white dry crystals (isolated product yield: 95 mole percent). The reduced coenzyme $Q_{10}$/oxidized coenzyme $Q_{10}$ weight ratio of the obtained crystal was 99.3/0.7, and the purity of reduced coenzyme $Q_{10}$ was 99.0%.

EXAMPLE 11

Reduction and concentration were carried out in the same manner as in Example 7 except that 15 g of zinc power and 1100 g of 2.9 N sulfuric acid were used as the reducing agent instead of sodium dithionite. The obtained oily reduced coenzyme $Q_{10}$ was easily stirred and brushed away. The oily reduced coenzyme $Q_{10}$/oxidized coenzyme $Q_{10}$ weight ratio was 99.4/0.6. The residual amount of heptane was 1.9% and the purity of reduced coenzyme $Q_{10}$ without heptane was 99.1%.

EXAMPLE 12

Oxidized coenzyme $Q_{10}$ (100 g; purity 99.4%) and 60 g of L-ascorbic acid were added to 1000 g of ethanol, and the reduction reaction was carried out with stirring at 50° C. After the lapse of 24 hours, the reaction mixture was cooled to 50° C. At the same temperature and under reduced pressure, ethanol was distilled off to give oily reduced coenzyme $Q_{10}$. This oily product was washed 6 times with 1000 g of deaerated saturated brine at 48° C., and 1000 g of acetone added thereto to give an acetone solution of reduced coenzyme $Q_{10}$. The reduced coenzyme $Q_{10}$/oxidized coenzyme $Q_{10}$ weight ratio in the solution was 99.5/0.5.

EXAMPLE 13

Oily reduced coenzyme $Q_{10}$ obtained in Example 7 was dripped on a plate (40° C.) on which the reduced coenzyme $Q_{10}$ own crystal being spread, then the oily product was rapidly solidified, and a solid in the hemisphere shape was obtained.

COMPARATIVE EXAMPLE 3

Oily reduced coenzyme $Q_{10}$ obtained in Example 7 was dripped on a plate (40° C.) on which no reduced coenzyme $Q_{10}$ own crystal being spread, and the temperature was maintained for 1 hour, but no solidification occurred.

REFERENCE EXAMPLE 1

One gram of reduced coenzyme $Q_{10}$ (reduced coenzyme $Q_{10}$/oxidized coenzyme $Q_{10}$ weight ratio=99.6/0.4) was dissolved in 20 g of each of various solvents shown in Table 1 at 25° C. After 24 hours of stirring at 25° C. in the air, the reduced coenzyme $Q_{10}$/oxidized coenzyme $Q_{10}$ weight ratio in each solution was determined. The results thus obtained are shown in Table 1.

TABLE 1

| Solvent | R |
| --- | --- |
| Heptane | 99.1/0.9 |
| Hexane | 98.7/1.3 |
| Toluene | 98.8/1.2 |
| Chloroform | 98.9/1.1 |
| Ethylacetate | 98.9/1.1 |
| Methyltert-butylether | 98.6/1.4 |
| Tetrahydrofuran | 98.5/1.5 |

R: Reduced coenzyme $Q_{10}$/Oxidized coenzyme $Q_{10}$ weight ratio

REFERENCE EXAMPLE 2

One gram of reduced coenzyme $Q_{10}$ (reduced coenzyme $Q_{10}$/oxidized coenzyme $Q_{10}$ weight ratio=99.6/0.4) was dissolved in 100 g of each of various solvents shown in Table 2 at 35° C. After 24 hours of stirring at 35° C. in the air, the reduced coenzyme $Q_{10}$/oxidized coenzyme $Q_{10}$ weight ratio in each solution was determined. The results thus obtained are shown in Table 2.

TABLE 2

| Solvent | R |
| --- | --- |
| Heptane | 96.7/3.3 |
| Ethylacetate | 96.4/3.6 |
| Acetonitrile | 96.0/4.0 |

R: Reduced coenzyme $Q_{10}$/Oxidized coenzyme $Q_{10}$ weight ratio

INDUSTRIAL APPLICABILITY

The present invention, which has the constitution described above, is a method superior in workability on a commercial scale and economic efficiency, and can give high-quality reduced coenzyme $Q_{10}$ in the form of oil, a crystal, slurry or a solution in a convenient and efficient manner.

The invention claimed is:

1. A method for obtaining reduced coenzyme $Q_{10}$ which comprises obtaining oily reduced coenzyme $Q_{10}$ from an organic phase containing reduced coenzyme $Q_{10}$ by distilling off an organic solvent at or above the melting temperature of reduced coenzyme $Q_{10}$, wherein the obtained oily reduced coenzyme $Q_{10}$ has the solvent content of 10% by weight or less.

2. The method according to claim 1, wherein the purity of reduced coenzyme Q10 existing in the organic phase is 80% by weight or more.

3. The method according to claim 1, wherein the organic solvent is distilled off at 40° C. or higher temperature.

4. The method according to claim 1 wherein a solution or slurry of reduced coenzyme Q10 is obtainable by adding a solvent to the obtained oily reduced coenzyme Q10.

5. The method according to claim 4, wherein the solvent to be added has a lower boiling point than that of the organic solvent to be distilled off.

6. The method according to claim 4, wherein the solvent to be added forms an azeotrope with the organic solvent to be distilled off.

7. The method according to claim 4, wherein the solvent to be added contains a hardly volatile component.

8. The method according to claim 1 wherein the organic phase containing reduced coenzyme Q10 is obtainable by reducing the organic phase containing oxidized coenzyme Q10 using a reducing agent.

9. The method according to claim 8, wherein the reducing agent is dithionous acid or a salt thereof or an ascorbic acid or a related compound thereof.

10. The method according to claim 4, wherein the solvent to be added has a less ability to protect reduced coenzyme Q10 from oxidization than the organic solvent to be distilled off.

11. The method according to claim 1 wherein the organic solvent to be distilled off is at least one species selected from the group consisting of hydrocarbons, fatty acid esters, ethers and nitriles.

12. The method according to claim 4, wherein the solvent to be added is an alcohol.

13. The method according to claim 4, wherein the solvent to be added is a ketone.

14. The method according to claim 1, wherein solid reduced coenzyme Q10 is obtainable by contacting a seed crystal of reduced coenzyme Q10 with the obtained oily reduced coenzyme Q10 at a temperature below the melting temperature of said oily reduced coenzyme Q10 followed by solidifying said oily reduced coenzyme Q10.

15. The method according to claim 1 which is carried out under a deoxygenated atmosphere.

* * * * *